US009658474B2

(12) United States Patent
Sheldon et al.

(10) Patent No.: US 9,658,474 B2
(45) Date of Patent: May 23, 2017

(54) EYEWEAR FRAME HAVING VENTS

(71) Applicant: Brent Sheldon, Miami Beach, FL (US)

(72) Inventors: Brent Sheldon, Miami Beach, FL (US); Thomas Rouayroux, Montreal (CA); Antoine Dallaire, Montreal (CA)

(73) Assignee: Brent Sheldon, Miami Beach, FL (US)

( * ) Notice: Subject to any disclaimer, the term of this patent is extended or adjusted under 35 U.S.C. 154(b) by 131 days.

(21) Appl. No.: 14/638,347

(22) Filed: Mar. 4, 2015

(65) Prior Publication Data

US 2016/0259184 A1 Sep. 8, 2016

(51) Int. Cl.
| | |
|---|---|
| G02C 11/08 | (2006.01) |
| B29C 39/02 | (2006.01) |
| B29C 39/12 | (2006.01) |
| A61F 9/02 | (2006.01) |
| B29L 12/00 | (2006.01) |

(52) U.S. Cl.
CPC .............. *G02C 11/08* (2013.01); *A61F 9/028* (2013.01); *B29C 39/02* (2013.01); *B29C 39/123* (2013.01); *B29K 2995/007* (2013.01); *B29L 2012/005* (2013.01); *G02C 2200/08* (2013.01)

(58) Field of Classification Search
CPC .......... G02C 5/00; G02C 5/001; G02C 5/006; G02C 5/008; G02C 5/02; G02C 5/04; G02C 5/06; G02C 5/08; G02C 5/10
USPC ......... 351/62, 41, 83, 85–88, 103, 105–107, 351/109
See application file for complete search history.

(56) References Cited

U.S. PATENT DOCUMENTS

| | | | |
|---|---|---|---|
| 5,239,320 A | 8/1993 | Allendorf et al. | |
| 5,576,775 A | 11/1996 | Bolle | |
| 5,638,145 A | 6/1997 | Jannard et al. | |
| 5,815,235 A | 9/1998 | Runckel | |
| 6,550,914 B1 | 4/2003 | Kopfer | |
| 6,959,988 B1 | 11/2005 | Sheldon | |
| 7,325,919 B2 | 2/2008 | Sheldon | |
| 8,047,649 B2 | 11/2011 | Chen | |
| 8,348,420 B2 | 1/2013 | Li | |
| 2003/0081169 A1 | 5/2003 | Kopfer | |
| 2005/0213025 A1* | 9/2005 | Lane ...................... | G02C 11/08 351/62 |
| 2011/0001921 A1 | 1/2011 | Matera | |
| 2011/0122364 A1* | 5/2011 | Yang ...................... | A61F 9/025 351/154 |
| 2012/0169989 A1 | 7/2012 | Lin | |

OTHER PUBLICATIONS

International Search Report and Written Opinion for PCT/US2016/019537 dated May 9, 2016, 11 pages.

* cited by examiner

Primary Examiner — Ricky Mack
Assistant Examiner — Robert E Tallman
(74) Attorney, Agent, or Firm — Klintworth & Rozenblat IP LLC (57) ABSTRACT

An eyewear frame structure for holding at least one lens thereto, includes a base frame, a front frame attached to a front of the base frame and a comfort bar attached to a back side of the base frame. The frame structure has a plurality of vent passages extending therethrough. Each vent passage includes a substantially horizontal section defined between the base frame and the front frame, and a substantially vertical section defined between the base frame and the comfort bar.

13 Claims, 6 Drawing Sheets

EYEWEAR FRAME HAVING VENTS

TECHNICAL FIELD

The application relates generally to eyewear, and more particularly to an eyewear frame structure having vents and a method for making same.

BACKGROUND OF THE ART

Eyewear including eyeglasses and goggles for various purposes conventionally include a frame structure made of substantially rigid material such as a rigid plastic material, with one or two lenses attached thereto. The frame structure is used to support the lens or lenses thereon and is configured in accordance with, and abuts the eyewear users face around or near the eyes. The frame structure is retained on the users head by a side piece or pieces, for example, temples or an elastic strap. Some eyewear such as eyeglasses or goggles for sports or safety, may suffer to some degree from fogging of the lens or lenses due to the perspiration and warmth emanating from the user's face. To solve this problem, manufacturers of eyewear have included vents in the eyewear frame structure to allow moisture and heat to escape from the space between the eyewear and the user's face. Efforts have been made to design vent structures which prevent foreign substances such as dust and liquids from flying through the vents and impacting the user's face or even entering the user's eyes. In addition, modern eyewear requires eyewear frame structures in complicated geometries and may be made of more than one material, which presents additional challenges for eyewear manufacturers to provide vents in such modern eyewear frame structures.

Therefore, there is a need for improved eyewear frame structures having vents which allow ventilation but prevent foreign particles from being carried in the airflow to impact on a user's eyes and face.

SUMMARY

In one aspect, there is provided an eyewear frame structure for holding at least one lens thereto, the eyewear frame structure comprising: a base frame including an upper member extending between opposed ends of the base frame, and defining a groove in the front side of the upper member thereof, the groove extending along a length of the upper member; a front frame including an elongate member attached to a front side of the upper member of the base frame, the elongate member of the front frame being partially received in the groove of the base frame; a comfort bar attached to a back side of the base frame; and a plurality of vent passages extending through the frame structure, each of the vent passages including a substantially horizontal section defined between the base frame and the front frame and a substantially vertical section defined between the base frame and the comfort bar.

In another aspect, there is provided a method for making an eyewear frame structure, comprising steps of: a) molding a base frame structure including an upper member extending between opposed ends thereof with a plurality of passageways extending therethrough between front and rear sides of the upper member, each of the passageways defining an opening on the respective front and rear sides of the upper member; and b) with the presence of the molded base frame, molding a front frame attached to the front side of the upper member of the base frame and molding a comfort bar attached to the back side of the upper member of the base frame, the front frame defining a plurality of recesses aligning with the respective passageway openings on the front side of the upper member of the base frame and the comfort bar partially covering each passageway opening on the back side of the upper member of the base frame, thereby forming a plurality of vent passages, each of the vent passages including a substantially horizontal section defined between the base frame and the front frame and a substantially vertical section defined between the base section and the comfort bar.

DESCRIPTION OF THE DRAWINGS

Reference is now made to the accompanying drawings in which.

It will be noted that throughout the appended drawings, like features are identified by like reference numerals.

It should also be noted that throughout the following description and claims, the terms "front"/"forward" and "back"/"rearward"("rear") refer to directions from the perspective of the user—i.e. further away from the user's face is referred to as "front" or "forward" and closer to the user's face is referred to as "back" or "rear".

DETAILED DESCRIPTION

Figure 1:
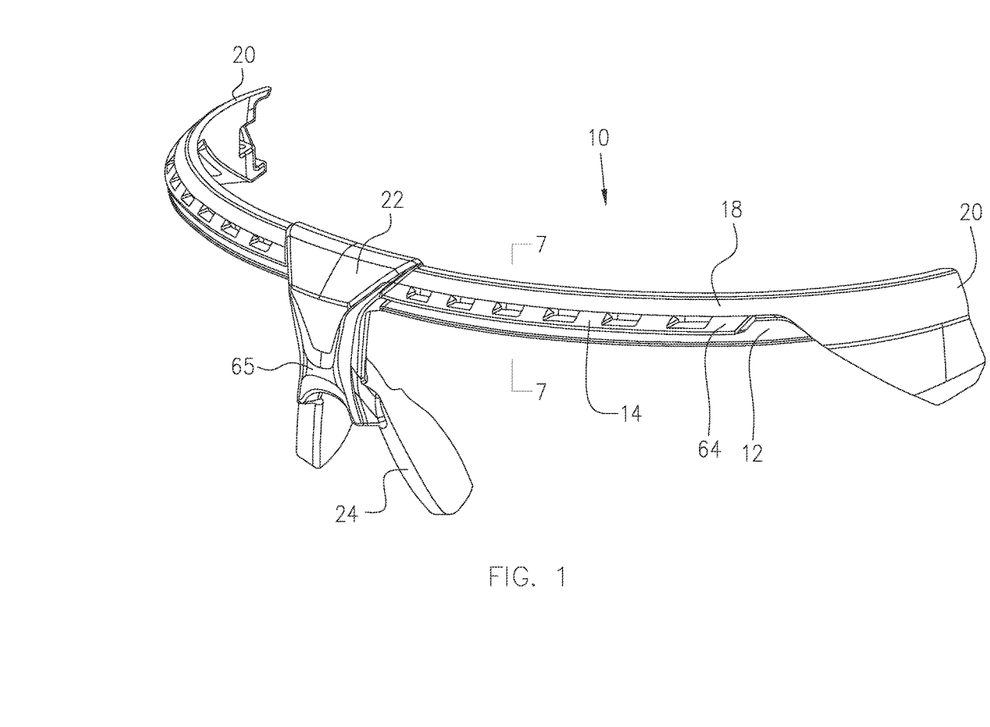
FIG. 1 is a front perspective view of an eyewear frame structure according to one embodiment.
Figure 2:
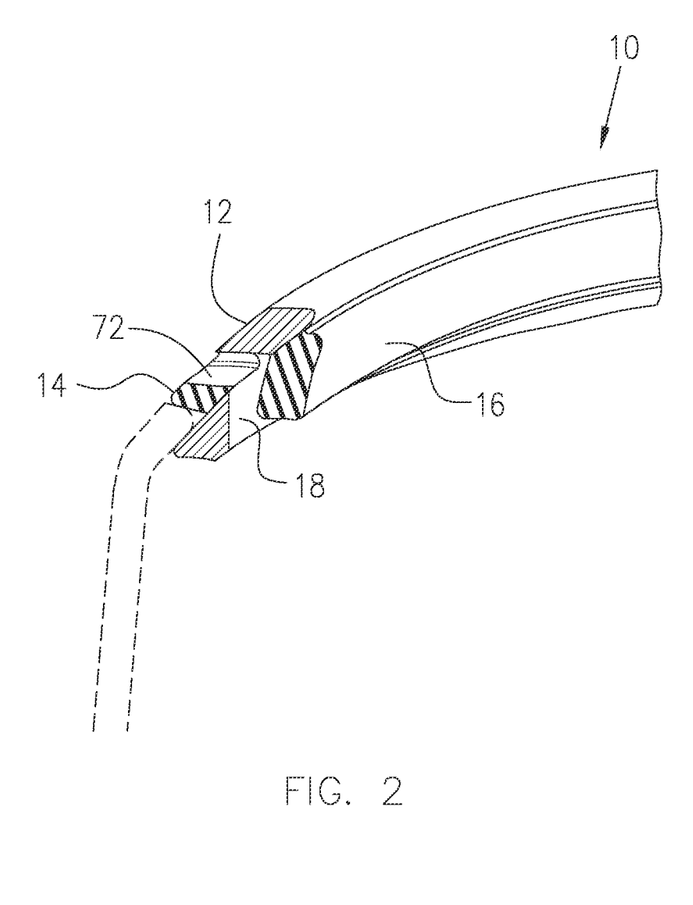
FIG. 2 is a partial rear perspective view of the frame structure of FIG. 1 with a section thereof cut away along line 7-7 of FIG. 1, showing a vent passage thereof.
Figure 3:
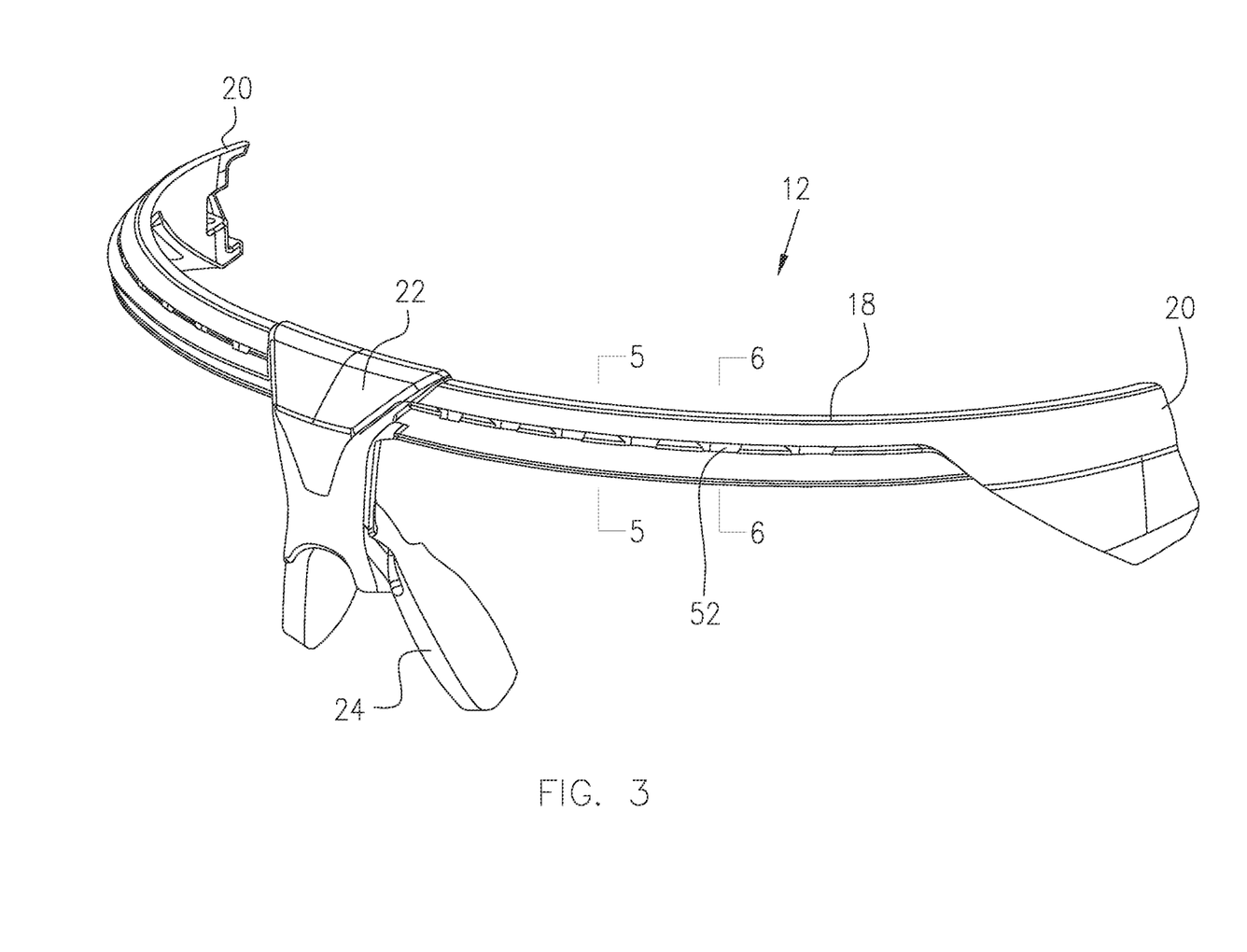
FIG. 3 is a front perspective view of a base frame of the frame structure of FIG. 1.
Figure 4:
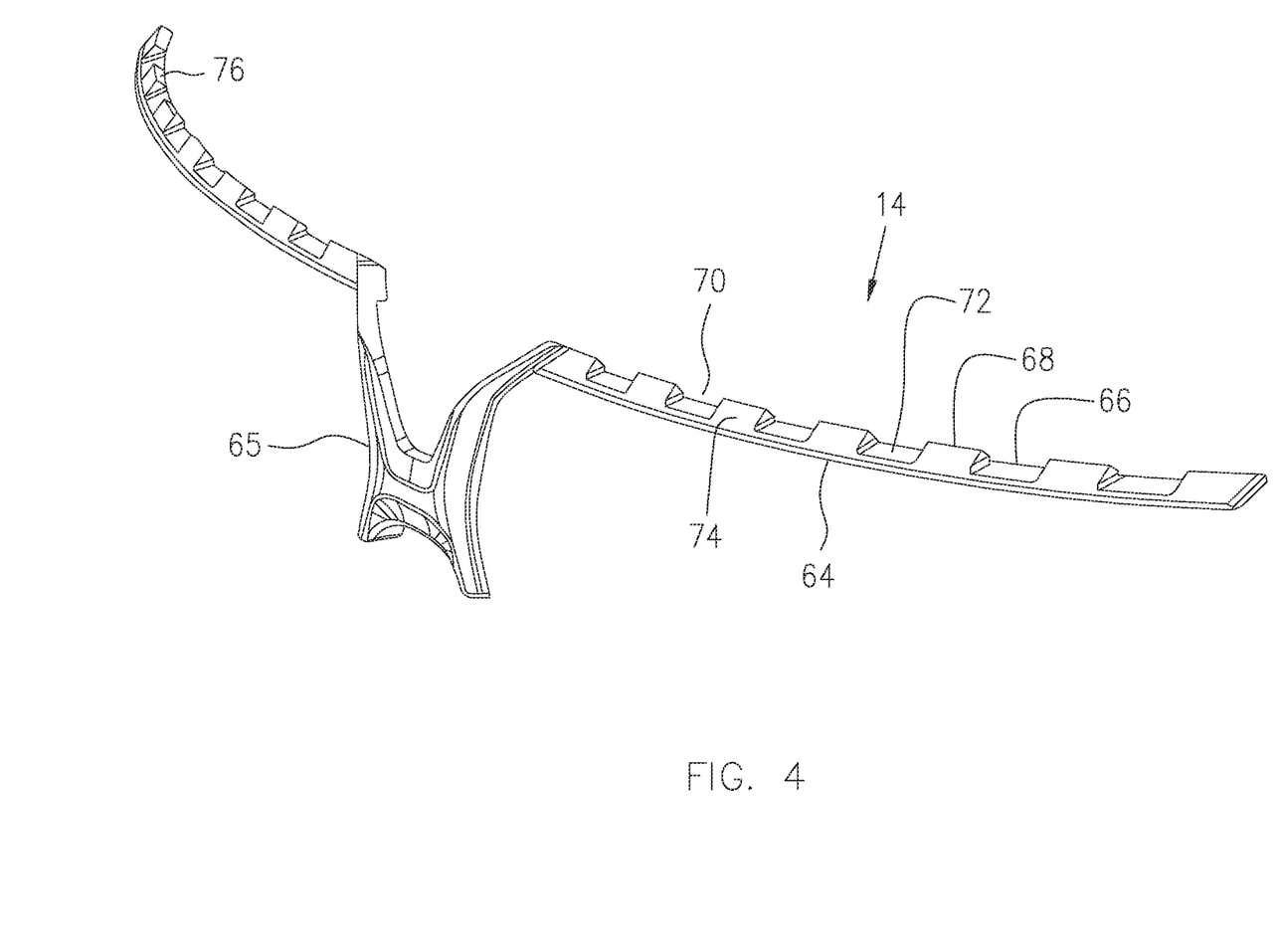
FIG. 4 is a front perspective view of a front frame of the frame structure of FIG. 1.
Figure 5:
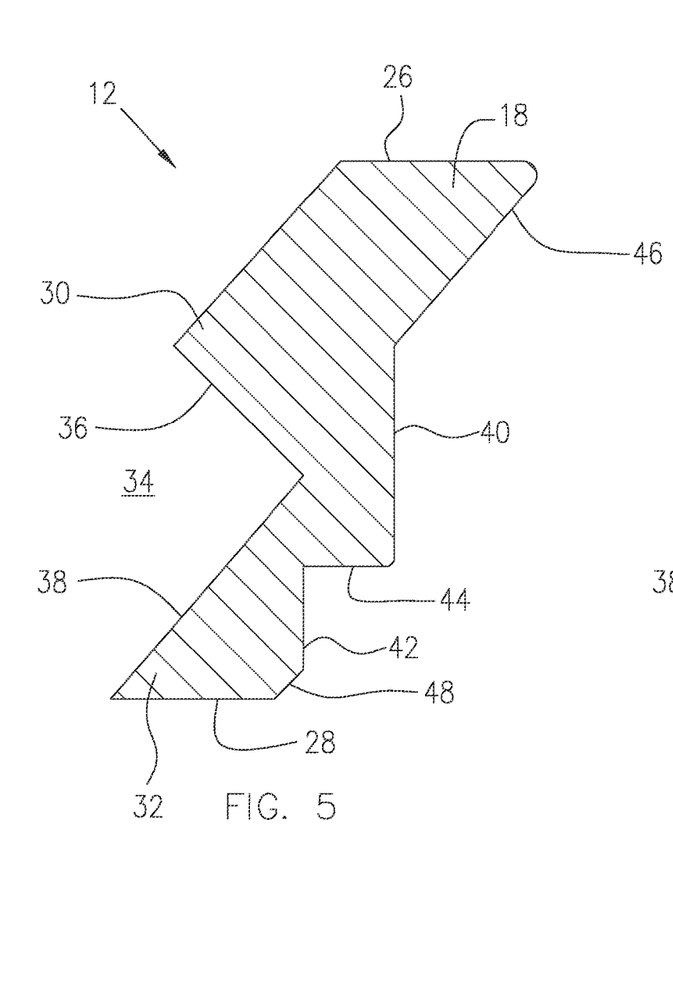
FIG. 5 is a cross-sectional view of the base frame taken along line 5-5 in FIG. 3, showing a cross-section of the base frame between adjacent vent passages.
Figure 7:
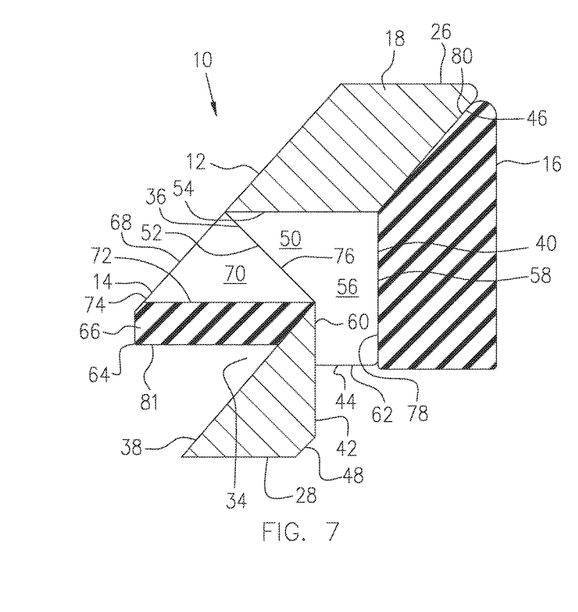
FIG. 7 is a cross-sectional view of the frame structure taken along line 7-7 in FIG. 1, showing the vent passage having a substantially horizontal section and a substantially vertical section.
Figure 8:
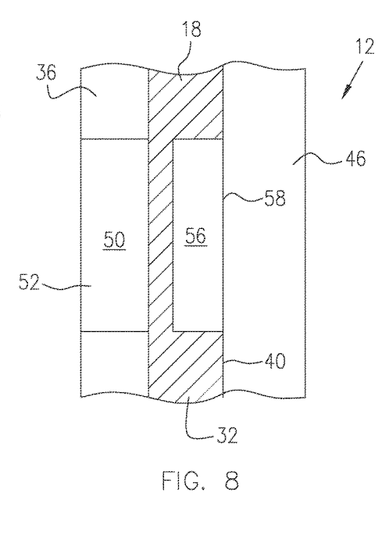
FIG. 8 is a cross-sectional view of the base frame taken along line 8-8 in FIG. 6, showing the back recess formed in the back side of the base frame.

FIGS. 1, 2 and 7 illustrate an eyewear frame structure 10 according to one embodiment, for holding at least one lens (shown in broken lines in FIG. 2) thereto. The eyewear frame structure 10 may include a base frame 12 of a substantially rigid plastic material, a front frame 14 attached to a front side (not numbered) of the base frame 12, and a comfort bar 16 attached to a back side of the base frame 12. The front frame 14 and comfort bar 16 may be made of a material that is flexible and soft relative to the rigid plastic material of the base frame 12. Such flexible and soft material may for example, be rubber. The frame structure 10 may be configured in a curvature suitable for being worn on a user's head.

Referring to FIGS. 1-3 and 5-8, the base frame 12 may include an upper member 18 extending between opposed ends 20 of the base frame 12, which may be configured with respective enlarged end sections (not numbered) for providing, for example, suitable pivotal connections to temples (not shown) of the eyewear, Optionally, the base frame 12 may include a connector 22 attached to a central portion of the upper member 18. The connector 22 may extend downwardly to support a pair of nose pieces 24 which are not part of the described subject matter and will not be further described hereinafter. The upper member 18 may therefore be formed as two similar sections, extending from the connector 22 toward the respective opposed ends 20. Due to the similarity of the two sections and for simplicity of description, only one section will be described in detail hereinafter.

The upper member 18 of the base frame 12 defines a front side (not numbered) between a top surface 26 and a bottom surface 28 thereof, facing away from a user's face. The upper member 18 also defines a back side (not numbered) thereof between the top and bottom surfaces 26, 28, facing toward the user's face. The front side of the upper member 18 may include an upper ridge 30 and a lower ridge 32. Both upper and lower ridges 30, 32 project forwardly and extend along a length of the upper member 18 between the connector 22 and the corresponding enlarged end section. A groove 34 which may have a triangular cross-section, may therefore be formed between the upper and lower ridges 30 and 32, and may extend along a length of the upper member 13, corresponding with the ridges 30, 32. The groove 34 may therefore be formed with an upper surface 36 and a lower surface 38 which in combination define the triangular cross-section of the groove 34.

The back side of the upper member 18 may include two substantially vertical surfaces (which are referred to as a first rear-facing surface 40 and a second rear-facing surface 42) and a downward-facing surface 44 which in combination define a shoulder (not numbered) extending along a length of the upper member 18 on the back side thereof. Inclining transitional surfaces 46, 48 may be provided between the top surface 26 and the first rear-facing surface 40 and between the bottom surface 28 and the second rear-facing surface 42, respectively. The first rear-facing surface 40 may define a vertical dimension from the inclining transitional surface 46 to the downward-facing surface 44

Figure 6:
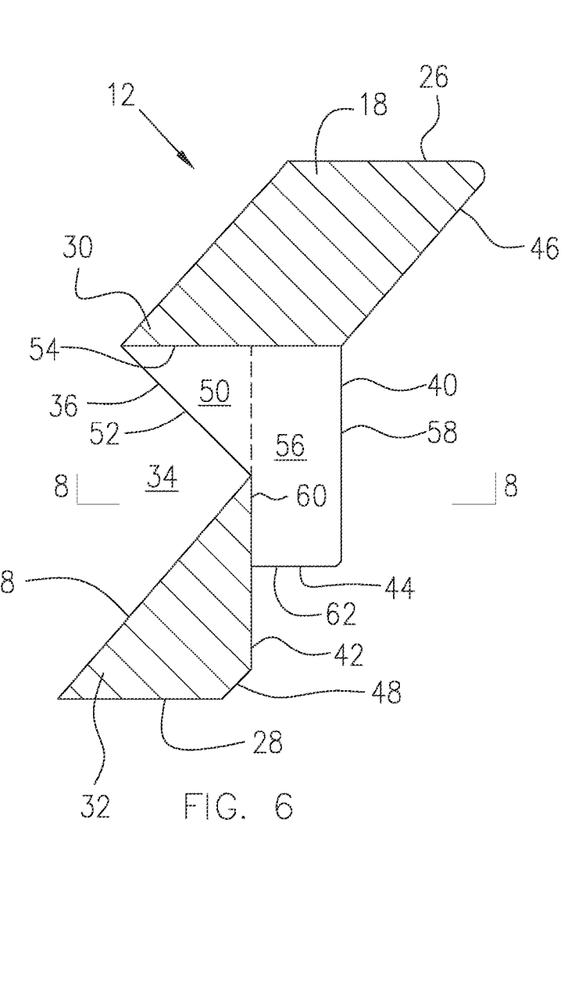
FIG. 6 is a cross-sectional view of the base frame taken along 6-6 in FIG. 3, showing front and back recesses in fluid communication with each other to provide structural features of the complete vent passage in the frame structure of FIG. 1.

The upper member 18 may define a plurality of spaced apart first recesses 50 in the groove 34 (see FIG. 6). Each first recess 50 may define an opening 52 (see FIGS. 3 and 6) on the upper surface 36 of the groove 34 and may be recessed rearwardly to define side surfaces (not numbered, see FIG. 8) and an upper surface 54 (see FIG. 6). Therefore, the first recess 50 may have a triangular cross-section as shown in FIG. 6.

The upper member 18 may further define a plurality of second recesses 56 on the back side thereof. Each second recess 56 may define an opening 58 on the first rear-facing surface 40 and may be recessed forwardly to define side surfaces (not numbered, see FIG. 8) and an inner surface 60. The second recess 56 may be configured to have a vertical dimension corresponding to the vertical dimension of the first rear-facing surface 40, resulting in formation of another opening 62 of the second recess 56 in the downward-facing surface 44.

The first recesses 50 may align with and be in fluid communication with respective second recesses 56. Therefore, a part of the inner surface 60 of the second recess 56 (as shown by broken lines in FIG. 6) may not exist and each first recess 50 and the corresponding second recess 56 in combination may form a passageway extending through the upper member 18 of the base frame 12 between the front and back sides thereof.

Referring to FIGS. 1-2, 4 and 7, the front frame 14 may include an elongate member 64. Optionally, the elongate member 64 may have symmetrical right and left sections (not numbered) joined together by a center piece 65 which may be configured to correspond with and be attached to the connector 22 of the base frame 12.

Each section of the elongate member 64 may include a flat strap 66 and a plurality of spacers 68 projecting upwardly from the flat strap 66 to define a plurality of recesses 70 between adjacent spacers 68. An upward-facing surface of the flat strap may form a bottom surface 72 of each recess 70. Each section of the elongate member 64 of the front frame 14 may be partially received in the triangular groove 34 defined in the front side of the base frame 12.

Each spacer 68 of the elongate member 64 may define a triangular cross-section including a front-facing surface 74 and rear-facing surface 76. The triangular cross-section of the spacer 68 may be configured such that the rear-facing surface 76 is in full contact with the upper surface 36 of the triangular groove 34 of the base frame 12. The plurality of recesses 70 defined between adjacent spacers 68 according to one embodiment, may align with the respective openings 52 (see FIG. 3) defined in the upper surface 36 of the triangular groove 34 in the base frame 12. Therefore, a plurality of substantially horizontal passage sections (not numbered) may be formed, each having a top surface defined by the upper surface 54 of the respective recess 50 (see FIGS. 6 and 7) in the base frame 12 and a bottom surface defined by the bottom surface 72 of the respective recess 70 of the flat strap 66 in the front frame 14. It should be noted that the substantially horizontal passage section defined between the upper surface 54 of the recess 50 and the bottom surface 72 of the recess 70, is in fluid communication with the second recess 56 (see FIG. 6) defined in the back side of the upper member 18 of the base frame 12.

The comfort bar 16 according to one embodiment may be attached to the back side of the upper member 18 of the base frame 12, having a length extending between and terminating at the two opposed enlarged end sections of the upper member 18. Optionally, the comfort bar 16 may comprise two sections corresponding to the respective sections of the elongate member 64 of the front frame 14.

The comfort bar 16 may be configured such that a front surface 78 of the comfort bar 16 is placed flat against the first rear-facing surface 40 of the upper member 18 of the base frame 12, and a top surface 80 of the comfort bar 16 is in full contact with the inclining transition surface 46 of the upper member 18. Therefore, the comfort bar 16 may partially cover the openings of the respective second recesses 56 (see FIGS. 6 and 7) that is, the comfort bar 16 only covers openings 58 of each recess 56 (defined in on the first rear facing surface 40), but does not block the opening 62 of the recesses 56 defined on the downward-facing surface 44 of the upper member 18. Therefore, each second recess 56 with the opening 62 may form a substantially vertical passage section (not numbered) between the inner surface 60 of the recess 56 in the base frame 12 and the front surface 78 of the comfort bar 16. The substantially horizontal passage section formed by the combination of the recesses 70 and 50 together with the substantially vertical passage section formed by the recess 56 are in fluid communication and therefore, in combination form an "indirect" or L-shaped vent passage (not numbered) extending through the frame structure 10. The "indirect" OR L-shaped vent passage therefore has an opening thereof on the front side of the frame structure 10 and an opening on the back side of the frame structure 10. Therefore, the "indirect" or L-shaped vent passage allows effective moisture venting and air circulation while preventing foreign particles which pass through the vent passages from entering the user's eyes and from impacting the user's face.

Referring to FIGS. 2 and 7, the elongate member 64 of the front frame 14 may be partially received in the triangular groove 34 in the upper member 18 of the base frame 12 such that the groove 34 is not fully filled by the elongate member 64. Therefore, a smaller triangular groove (not numbered) may be formed between a downward-facing surface 81 (the bottom) of the flat strap 66 of the elongate member 64 and the lower surface 38 of the triangular groove 34 in the upper member 18 of the base frame 12. This smaller triangular groove may form a retaining device for retaining an upper peripheral edge of the lens, such as illustrated in FIG. 2. The frame structure 10 may be provided with further retaining means for retaining the lens or lenses to be attached thereto according to the configuration of the one more lenses. However, this feature is not part of the described subject matter and will not be further described herein.

The above description is meant to be exemplary only, and one skilled in the art will recognize that changes may be made to the embodiments described without departing from the scope of the described subject matter. For example, the base frame and front frame may not have the respective connector and central member such that the grooves in the base frame and the elongate member of the front frame may not be divided into sections. The base frame may be configured to have front and back sides different from the above-described embodiments but may provide a suitable interface with respect to the front frame and comfort bar to form the vent passages defined therebetween. Modifications which fall within the scope of the described subject matter will be apparent to those skilled in the art, in light of a review of this disclosure, and such modifications are intended to fall within the appended claims.

The invention claimed is:

1. An eyewear frame structure for holding at least one lens thereto, the eyewear frame structure comprising:
 a base frame including an upper member extending between opposed ends of the base frame, and defining a groove in the front side of the upper member thereof, the groove extending along a length of the upper member;
 a front frame molded to the base frame and thereby integrally formed therewith, the front frame including an elongate member attached to a front side of the upper member of the base frame, the elongate member of the front frame being partially received in the groove of the base frame;
 a comfort bar molded to the base frame and thereby integrally formed therewith, the comfort bar disposed on a back side of the base frame; and
 a plurality of vent passages extending through the frame structure, each of the vent passages including a substantially horizontal section defined between the base frame and the front frame and a substantially vertical section defined between the base frame and the comfort bar, wherein the substantially horizontal section of the vent passage comprises a top surface defined on the base frame and a bottom surface defined on the front frame, and wherein the substantially vertical section of the vent passage comprises a front surface thereof defined on the base frame and a rear surface defined on the comfort bar.

2. The eyewear frame structure as defined in claim 1 wherein the elongate member of the front frame comprises a plurality of spacers projecting upwardly from the elongate member to define a plurality of recesses between adjacent spacers, each of the recesses having a bottom defining a bottom surface of the substantially horizontal section of the vent passage.

3. The eyewear as defined in claim 2 wherein the groove in the upper member of the base frame comprises a triangular cross section defining an upper surface and a lower surface of the groove, and wherein each of the spacers of the front frame comprises a triangular cross section defining a front-facing surface and a rear-facing surface, the rear-facing surface being in contact with the upper surface of the groove.

4. The eyewear frame structure as defined in claim 1 wherein the comfort bar extends between and terminates at two opposed end sections of the base frame.

5. The eyewear frame structure as defined in claim 1 wherein the upper member of the base frame defines a plurality of first recesses in the groove, each of the first recesses being recessed rearwardly to define an opening on the upper surface of the groove and having an upper surface, the upper surface defining a top surface of the substantially horizontal section of each vent passage.

6. The eyewear frame structure as defined in claim 5 wherein the upper member of the base frame defines a plurality of second recesses on the back side thereof, each of the second recesses being recessed forwardly to define an inner surface and an opening on respective rear-facing and downward-facing surfaces of the upper member of the base frame, the second recesses being in communication with the respective first recesses, the inner surface of the second recess defining a front surface of the substantially vertical section of each vent passage.

7. The eyewear frame structure as defined in claim 6 wherein the comfort bar covers the openings of the respective second recesses defined on the rear-facing surface, the openings of the second recesses defined on the downward-facing surface forming an opening of the substantially vertical section of the respective vent passages, a front surface of the comfort bar defining a rear surface of the substantially vertical section of each vent passage.

8. The eyewear frame structure as defined in claim 1 wherein the elongate member of the front frame and the upper member of the base frame in combination define a groove therebetween, the groove extending along a length of the frame structure for receiving a section of an upper edge of the at least one lens.

9. The eyewear as defined in claim 1 wherein the front frame and the comfort bar are flexible and soft relative to the base frame.

10. A method for making an eyewear frame structure, comprising steps of:
 a) molding a base frame structure including an upper member extending between opposed ends thereof with a plurality of passageways extending therethrough between front and rear sides of the upper member, each of the passageways defining an opening on the respective front and rear sides of the upper member; and
 b) with the presence of the molded base frame, molding a front frame to the front side of the upper member of the base frame and molding a comfort bar attached to the back side of the upper member of the base frame, the front frame defining a plurality of recesses aligning with the respective passageway openings on the front side of the upper member of the base frame and the comfort bar partially covering each passageway opening on the back side of the upper member of the base frame, thereby forming a plurality of vent passages, each of the vent passages including a substantially horizontal section defined between the base frame and the front frame and a substantially vertical section defined between the base section and the comfort bar, wherein the substantially horizontal section of the vent passage comprises a top surface defined on the base frame and a bottom surface defined on the front frame, and wherein the substantially vertical section of the vent passage comprises a front surface thereof defined on the base frame and a rear surface defined on the comfort bar.

11. The method as defined in claim 10 wherein the base frame is molded using a molding material which is rigid when cured, and wherein the front frame and the comfort bar are molded using a respective molding material which is flexible and soft relative to the rigid material of the base frame.

12. The method as defined in claim 11 wherein the front frame and the comfort bar are molded in one molding procedure using a same molding material.

13. The method as defined in claim 11 wherein the front frame and the comfort bar are molded in separate molding procedures using different molding materials.

* * * * *